`US009052274B2`

United States Patent
Depenheuer

(10) Patent No.: US 9,052,274 B2
(45) Date of Patent: Jun. 9, 2015

(54) LASER SPECTROMETER AND A METHOD FOR OPERATING A LASER SPECTROMETER

(71) Applicant: Siemens Aktiengesellschaft, Munich (DE)

(72) Inventor: Daniel Depenheuer, Schwegenheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/282,842

(22) Filed: May 20, 2014

(65) Prior Publication Data

US 2014/0347667 A1    Nov. 27, 2014

(51) Int. Cl.
| | |
|---|---|
| G01N 21/25 | (2006.01) |
| G01J 3/26 | (2006.01) |
| G01J 3/42 | (2006.01) |
| G01N 21/39 | (2006.01) |
| G01J 3/28 | (2006.01) |
| G01N 21/85 | (2006.01) |

(52) U.S. Cl.
CPC .............. *G01N 21/255* (2013.01); *G01J 3/26* (2013.01); *G01J 3/42* (2013.01); *G01N 21/39* (2013.01); *G01J 3/28* (2013.01); *G01N 21/85* (2013.01)

(58) Field of Classification Search
USPC .......................................... 356/300–334, 409
See application file for complete search history.

(56) References Cited

U.S. PATENT DOCUMENTS

| | | | |
|---|---|---|---|
| 4,241,997 A | 12/1980 | Chraplyvy | |
| 6,611,335 B1 * | 8/2003 | Hovde | ........................... 356/437 |

FOREIGN PATENT DOCUMENTS

WO    WO 2013045278 A1    4/2013

OTHER PUBLICATIONS

Aleksandra Foltynowicz: Characterization of Nonlinearities in Laser Frequency-To-Current Response in LDS6 for Improved Concentration Determination When Two Absorption Lines are Measured; 2007; Sep. 28, 2007.

(Continued)

*Primary Examiner* — Abdullahi Nur
(74) *Attorney, Agent, or Firm* — Cozen O'Connor

(57) ABSTRACT

A method for operating a laser spectrometer includes passing light of a semiconductor laser through a gas mixture containing a gas component and through an etalon structure onto a detector. The method also includes varying an injection current of the laser based on a predefined current-time function in order to tune the wavelength of the laser in a tuning range using a specific absorption line of the gas component. The method further includes modulating the function with a modulation signal having a frequency and alternately a first modulation amplitude and a second modulation amplitude. The method also includes evaluating a detector signal generated by the detector for determining (1) the concentration of the gas component upon the modulation with the first modulation amplitude and (2) the wavelength stabilization of the laser upon the modulation with the second modulation amplitude at the second harmonic of the frequency.

2 Claims, 3 Drawing Sheets

(56) References Cited

OTHER PUBLICATIONS

Aleksandra Foltynowicz: Procedure for Characterization on Nonlinearities in Laser Frequency Scan and Modulation Amplitude in LDS6; 2008; Dec. 16, 2008.

Kluczynski Pawel et al; "Theoretical description based on Fourier analysis of wavelength-modulation spectrometry in terms of analytical and background signals"; Applied Optics, Optical Society of America, Washington, DC; Bd. 38; Nr. 27; pp. 5803-5815; ISSN: 0003-6935; DOI: 10. 1364/AO.38.005803; XP 001176660;; 1999; Sep. 20, 1999.

* cited by examiner

LASER SPECTROMETER AND A METHOD FOR OPERATING A LASER SPECTROMETER

FIELD OF INVENTION

The invention relates to a laser spectrometer and to a method for operating the laser spectrometer.

DESCRIPTION OF THE RELATED ART

Laser spectrometers are used in particular for optical gas analysis in process metrology. In this case, a semiconductor laser, e.g., a laser diode, generates light, generally in the infrared range, which is passed through a gas mixture to be measured (process gas) and is subsequently detected. The intensity and wavelength of the light generated are nonlinear functions of the injection current and the operating temperature of the semiconductor laser. The wavelength of the light is tuned to a specific absorption line of that gas component of the process gas which is respectively to be measured, wherein the laser periodically samples the absorption line. For this purpose, the laser is driven with a predefined, preferably ramped or triangular, current-time function. The concentration of the gas component of interest can be determined from the detected absorption in the region of the absorption line.

In order to increase the measurement accuracy it is known to modulate the current-time function with a periodic, e.g., sinusoidal, modulation signal having the frequency "f" (a.k.a., wavelength modulation spectroscopy (WMS)) and to evaluate the detector signal at the doubled frequency 2f phase-sensitively (second harmonic detection).

On account of changes in the ambient conditions (e.g., the ambient temperature, drift in the drive electronics of the semiconductor laser, and/or deviations in the temperature measurement of the semiconductor laser), the wavelength of the light generated can vary to such a great extent that the evaluation of the absorption line is impaired. For this reason, a wavelength referencing (also called wavelength stabilization) is generally required.

For this purpose, by way of example, a reference cuvette with a reference gas contained therein can additionally be introduced into the light path and an absorption line of the reference gas can be measured. The temperature of the semiconductor laser can then be regulated using the position of the absorption line of the reference gas in such a way that the absorption line of the gas component to be measured is always at a specific location of the current-time function. In this case, the current ramp has to be great enough in order that the resultant tuning range of the semiconductor laser comprises both the absorption line of the gas component to be measured and that of the reference gas, or a suitable reference gas must be available whose absorption line lies spectrally in the vicinity of the absorption line of the gas component to be measured, such that it is attainable for the semiconductor laser.

Upon sufficiently great absorption, the absorption line of the gas component to be measured itself can also be used for the wavelength stabilization, by its actual position relative to the current-time function being compared with the desired position and the deviation being used for regulating the temperature of the semiconductor laser. The disadvantage of this method is that no regulation can be carried out at low concentrations of the gas component to be measured or upon the absence thereof. This is the case in particular in applications in which the absence of a specific gas component, which is normally not, permitted to be present, is monitored. The emission wavelength of the semiconductor laser could then drift such that, with an incorrect wavelength, an absence (zero concentration) of the gas component is detected, even though the gas component is present.

It is also known to split the laser beam into a measurement beam through the gas mixture to be measured and a reference beam through a cuvette filled with the gas component to be measured or a reference gas, and subsequently to detect both beams separately. This has the advantage that the detector signal generated from the reference beam for determining the wavelength deviation is free of all influences of the gas mixture to be measured. However, splitting the laser beam requires additional optical elements in the beam path (beam splitter), which can disturb the actual measurement beam and impair the sensitivity of the spectrometer. Furthermore, the additional detector for the reference beam leads to an increased technical outlay on apparatus.

The wavelength stabilization using a reference gas can be problematic if the reference gas is, e.g., highly toxic, corrosive or explosive and, consequently, the operation and transport of the laser spectrometer are restricted. It is possible to use an etalon instead of the reference gas for wavelength stabilization.

International Patent Application Publication No. WO 2013/045278 A1 discloses the use of an etalon for setting or adjusting the tuning range, i.e., the amplitude of the current-time function or height of the current ramp, of a laser spectrometer. Laser spectrometers have to be set or adjusted with regard to the wavelength and the tuning range for the first time during their production. The etalon serving for adjusting the tuning range and a gas cell, which serves for adjusting the wavelength and which is filled with a reference gas, are arranged one behind the other in the light path between semiconductor laser and detector. The free spectral range of the etalon is chosen such that it differs from the width of the absorption line of the reference gas.

When the wavelength is adjusted, the modulation amplitude of the modulation signal is adapted to the width of the absorption line of the reference gas. Thus, the detector signal is optimized for the detection of the absorption line, while the signal component of the etalon is greatly suppressed. For adjusting the tuning range, by contrast, the modulation amplitude is adapted to the free spectral range of the etalon. Thus, the detector signal is optimized for the detection of the transmission spectrum of the etalon. Since the absorption line of the reference gas is much wider, its signal component is suppressed and a virtually undisturbed transmission spectrum of the etalon is obtained.

SUMMARY OF THE INVENTION

The invention is therefore based on an object of enabling a wavelength stabilization using simple techniques during the normal measurement operation of a laser spectrometer. The object is achieved according to a laser spectrometer and a method for operating a laser spectrometer of the claimed invention.

The laser spectrometer is therefore operated in such a way or adapted to the effect that the light of a wavelength-tunable semiconductor laser is passed through a gas mixture containing a gas component to be measured and through an etalon structure onto a detector. The injection current of the semiconductor laser is varied periodically in accordance with a predefined current-time function in order to tune the wavelength of the semiconductor laser in a tuning range completely using a specific absorption line of the gas component, wherein the current-time function is modulated with a modulation signal having a frequency and alternately a first modulation amplitude adapted to the full width at half maximum of the absorption line and a second modulation amplitude greater by a multiple.

The detector signal generated by the detector is evaluated for determining the concentration of the gas component to be measured in the gas mixture upon the modulation with the first modulation amplitude and for the wavelength stabilization of the semiconductor laser upon the modulation with the second modulation amplitude at the second harmonic of the frequency, wherein the etalon structure either has a single etalon, the free spectral range of which is greater than the tuning range and less than double the tuning range, and the second modulation amplitude is adapted to the free spectral range of the etalon structure, or, in the alternative, the etalon structure contains at least two different etalons, the free spectral ranges of which are chosen in each case to be less than the tuning range such that the amplitude of the transmission function of each of the etalons, the dependence of which on the modulation amplitude approximately follows a Bessel function of the first kind and second order, is at least approximately zero at the first modulation amplitude.

In a method according to the invention, therefore, the wavelength stabilization is effected with the aid of an etalon structure and the modulation of the current-time function with the second modulation amplitude.

If the etalon structure comprises an individual etalon, then the free spectral range thereof is chosen to be greater than the tuning range and less than twice the tuning range of the semiconductor laser such that upon the tuning of the semiconductor laser only a maximum or minimum of the transmission spectrum of the etalon is visible to the detector. The second modulation amplitude is adapted to the free spectral range of the etalon structure such that the detection of the maximum or minimum is optimized, while the detected signal component of the absorption line of the gas component is suppressed. The wavelength stabilization is effected on the basis of the detected maximum or minimum.

By contrast, the absorption line of the gas component to be measured is detected during the modulation of the current-time function with the first modulation amplitude. Since the first modulation amplitude is adapted to the full width at half maximum of the absorption line and is less than the second modulation amplitude by a multiple, the detection of the absorption line is optimized, while the signal component of the etalon is greatly suppressed.

If the etalon structure contains at least two different etalons, then the free spectral ranges thereof are chosen in each case to be less than the tuning range and furthermore such that the amplitude of the transmission function of each of the etalons, the dependence of which on the modulation amplitude approximately follows a Bessel function of the first kind and second order, is at least approximately zero at the first modulation amplitude. Here, too, the detection of the absorption line of the gas component to be measured is optimized with simultaneous suppression of the signal component of the etalon because, on the one hand, the first modulation amplitude is adapted to the full width at half maximum of the absorption line and, on the other hand, the transmission functions of the etalons in the case of the first modulation amplitude have zeros.

As far as the wavelength stabilization with the aid of the etalon structure and upon modulation with the second modulation amplitude is concerned, then, owing to the small free spectral ranges of the etalons, a multiplicity of periods of their respective transmission spectra, i.e., a multiplicity of maxima and minima, are visible to the detector. Since the etalons are different and, as is explained in greater detail later, the zeros of the Bessel function mentioned are not rational multiples of one another, the detected transmission spectrum of the etalon structure, which results from the superimposition of the transmission spectra of the individual etalons, is not periodic. Therefore, over the tuning range this results in an unambiguously identifiable maximum or minimum in the transmission spectrum of the etalon structure, which cannot be confused with other maxima or minima and can therefore be used for the wavelength stabilization.

BRIEF DESCRIPTION OF THE DRAWINGS

For further explanation of the invention, reference is made below to the figures of the drawing, in which specifically.

DETAILED DESCRIPTION OF THE PRESENTLY PREFERRED EMBODIMENTS

Figure 1:
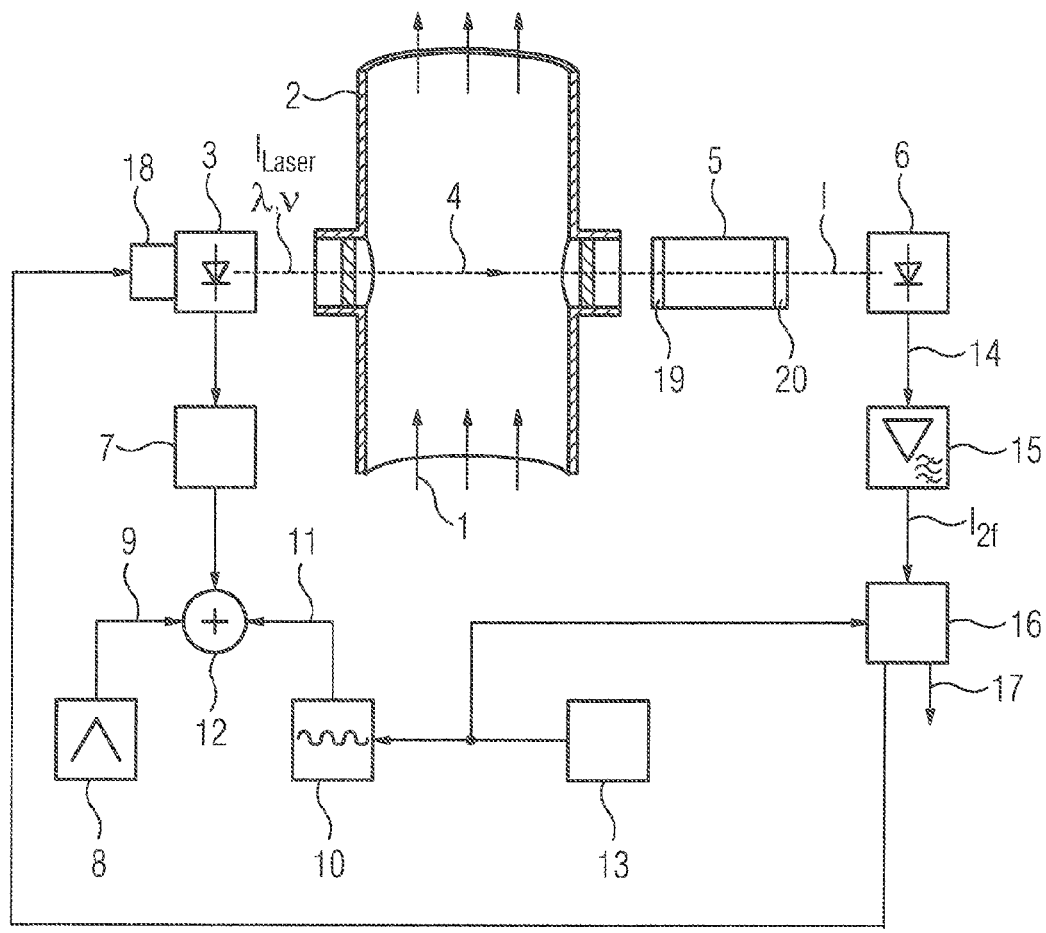
FIG. 1 shows a laser spectrometer in accordance with one embodiment of the present invention.

FIG. 1 shows in a schematic illustration a laser spectrometer for measuring the concentration of at least one gas component of interest in a gas mixture 1, which is contained in a measurement volume 2 and flows through a process gas line, for example. The spectrometer contains a semiconductor laser 3 in the form of a laser diode, the light 4 of which is incident through the gas mixture 1 and an etalon structure 5 on a detector 6. The semiconductor laser 3 is driven by a controllable current source 7 with an injection current i, wherein the intensity $I_{Laser}$ and wavelength λ of the light 4 generated are dependent on the current i and the operating temperature of the semiconductor laser 3.

The current source 7 is driven by a first signal generator 8 periodically with a preferably triangular or ramped signal 9, in order to vary the injection current i equally (current-time function). A second signal generator 10 generates a sinusoidal modulation signal 11 having the frequency f, with which the current-time function 9 is modulated in a summing element 12. The amplitude of the modulation signal 11 can be set using a control device 13.

On account of the driving of the laser 3 with the current-time function 9, the wavelength λ (or frequency ν) of the light 4 generated is varied periodically within a tuning range and a selected absorption line of the gas component of interest is sampled in a wavelength-dependent manner in this case. During the tuning of the semiconductor laser 3, the wavelength λ of the light 4 is simultaneously modulated with the frequency f on account of the modulation signal 11. During the sampling of the absorption line, the latter absorbs a small part of the light 4. The detector 6 generates a detector signal 14 in a manner dependent on the detected light intensity I, the second harmonic (2f signal component) $I_{2f}$ of which detector signal is amplified in a frequency-selective amplifier 15 and processed further phase-sensitively (lock-in) in a downstream evaluation device 16 and is evaluated to form a measurement result 17 indicating the concentration of the gas component of interest in the gas mixture 1.

In order to optimize the detection of the absorption line, the control device 13 sets the amplitude of the modulation signal 11 such that the modulation amplitude, i.e., the wavelength excursion Δλ (or frequency excursion Δλ) of the light 4 generated is adapted to the width, e.g., full width at half maximum (FWHM), of the absorption line to be sampled. In this regard, for the ideal case of a Lorentzian absorption line, the 2f signal component $I_{2f}$ becomes maximal in the case of a modulation index m of $m_{max}$=2.2 (the modulation index in is the ratio of the spectral modulation amplitude Δλ (or Δν) to the full width at half maximum of the sampled absorption line). By way of example, the semiconductor laser 3 is tuned for sampling an approximately 1 GHz wide absorption line over a range of 20 GHz in the case of a modulation Δν=2 GHz.

The etalon structure 5 serves to generate a detectable reference wavelength, on the basis of which the wavelength λ of the semiconductor laser 3 is calibrated and stabilized by virtue of the temperature thereof being regulated using a temperature regulator 18 or an offset for the current i being set. In the exemplary embodiment shown, the etalon structure 5 comprises an individual etalon having two plane-parallel partly mirrored windows 19, 20, between which the light 4 is reflected back and forth. On account of multiple interferences, the intensity I of the emerging light varies periodically with the change in the laser wavelength λ. In this case, the period length corresponds to the free spectral range (FSR) of the etalon 5, while the number of periods is a measure of the change in the wavelength λ over the tuning range of the semiconductor laser 3.

Figure 2:
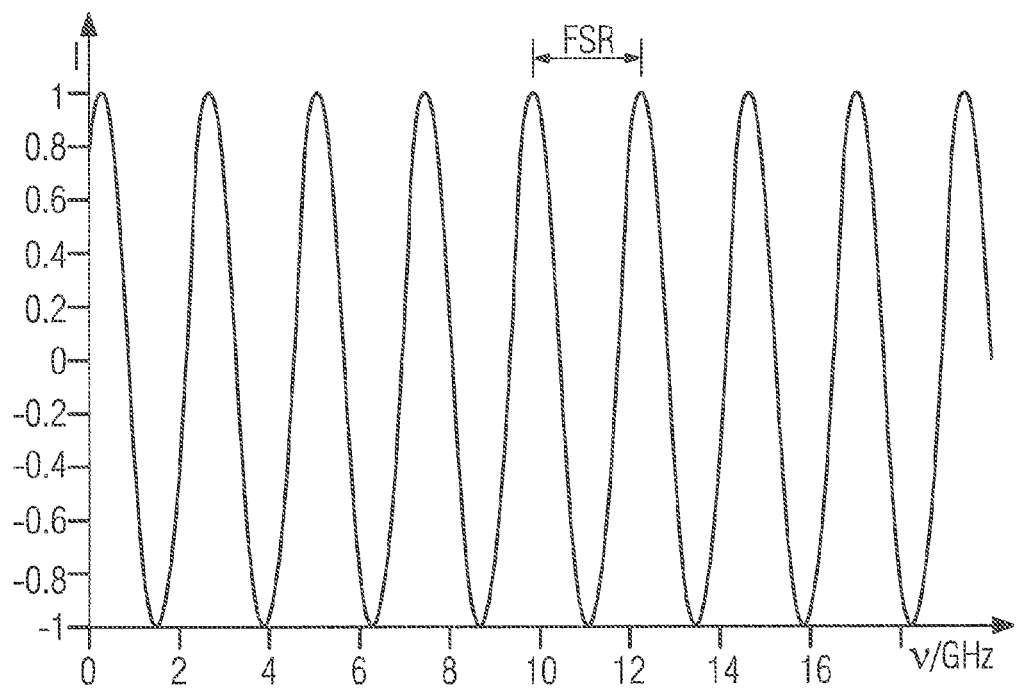
FIG. 2 shows one example of the transmission spectrum of an etalon of its free spectral range being less than the tuning range of the laser spectrometer in accordance with one embodiment of the present invention.

FIG. 2 shows one example of the transmission spectrum of an etalon of the free spectral range FSR being less than the tuning range. The intensity I of the light 4 emerging from the etalon (in arbitrary units) is plotted against the tuning range of the wavelength λ or frequency ν. The above-mentioned tuning range of 20 GHz and a free spectral range of 2.4 GHz are used as a numerical example.

The wavelength λ of the laser 3 can be stabilized on the basis of a maximum or minimum of the transmission spectrum, but the detection of such a maximum or minimum is made more difficult by its periodicity. A further problem is that the absorption line of the gas component of interest in the gas mixture 1 and the transmission spectrum of the etalon structure 5 are superimposed and thus mutually disturb one another for their respective detection.

With regard to the first-mentioned problem, in accordance with a first solution variant, the free spectral range FSR of the etalon 5 is chosen to be greater than the tuning range and less than double the tuning range, such that at least one maximum or minimum but also not more than this one maximum or minimum of the transmission spectrum of the etalon 5 is visible.

Figure 3:
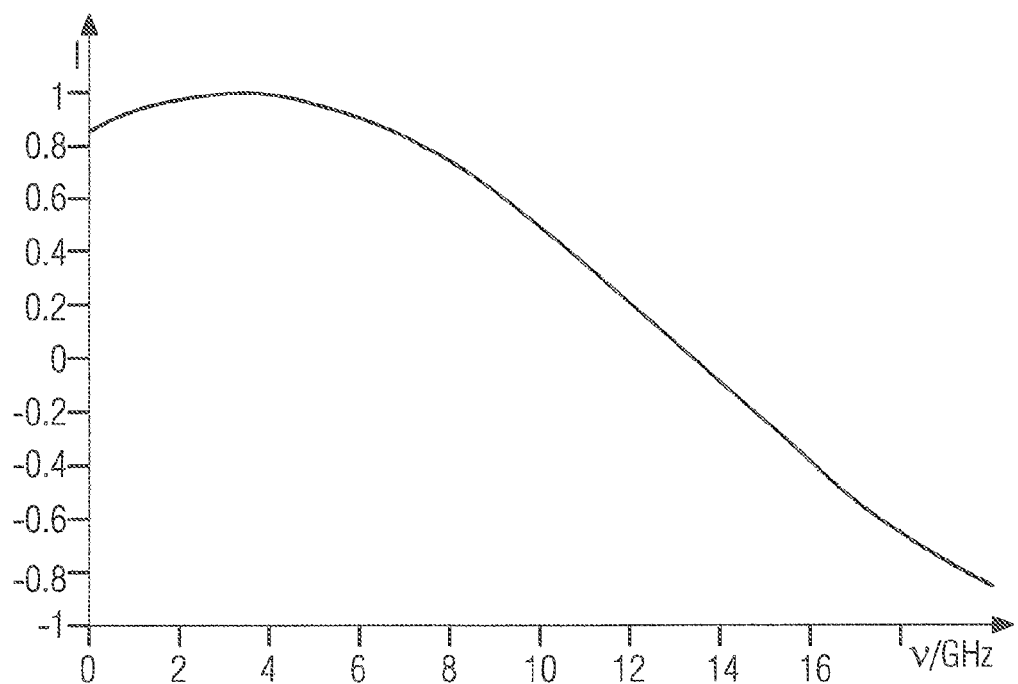
FIG. 3 shows one example of the transmission spectrum of an etalon of its free spectral range being greater than the tuning range and less than double the tuning range in accordance with one embodiment of the present invention.

FIG. 3 shows one example of the transmission spectrum of the etalon 5, in which, proceeding from the above-mentioned tuning range of 20 GHz, the free spectral range is 40 GHz. The transmission function of the etalon 5 is dependent on the modulation amplitude Δλ or λν and follows a Bessel function $J_2(2\pi \cdot \Delta\nu/FSR)$ of the first kind and second order having zeros at Δν/FSR=0.83, 1.34, 1.85, etc.

Figure 4:
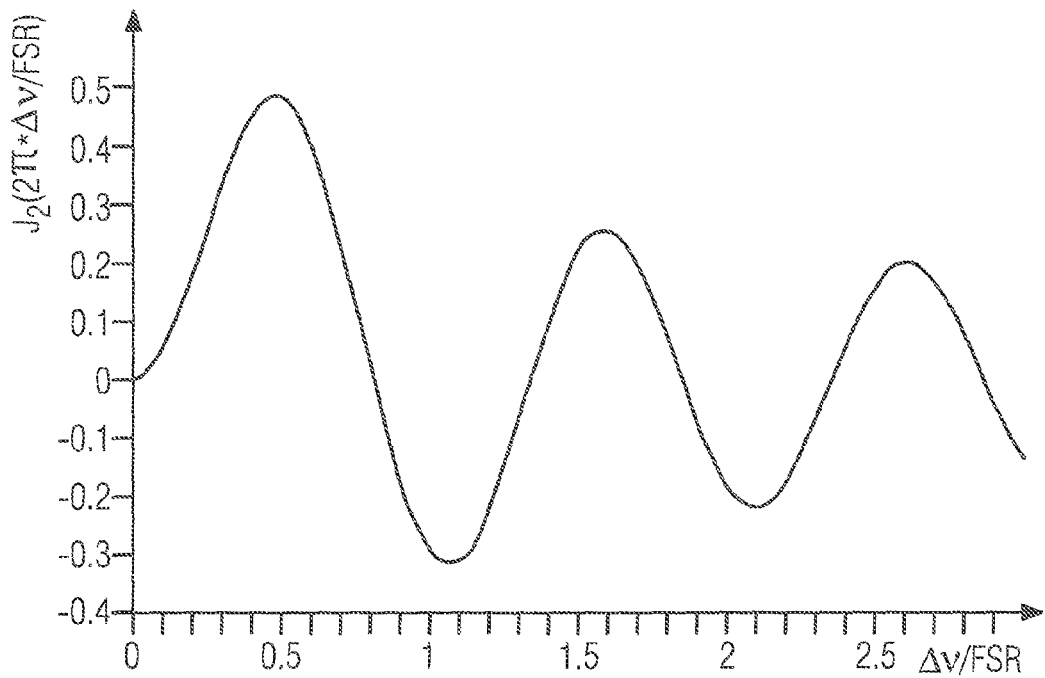
FIG. 4 shows a Bessel function of the first kind and second order in accordance with one embodiment of the present invention.

FIG. 4 shows such a Bessel function. In order to optimize the detection of the maximum of the transmission spectrum of the etalon 5 as shown in FIG. 3, the control device 13 (shown in FIG. 1) sets the amplitude of the modulation signal 11 such that the modulation amplitude, i.e., the wavelength excursion Δλ or frequency excursion Δν, of the light 4 generated is adapted to the free spectral range FSR=40 GHz of the etalon 5. In the example shown here, this is achieved with a modulation Δν=20 GHz, such that with Δν/FSR=0.5 the 2f signal component $I_{2f}$ of the detected maximum of the transmission function of the etalon 5 is maximal. As can easily be ascertained with reference to FIG. 4, the detected 2f signal component $I_{2f}$ of the transmission spectrum of the etalon 5 is greatly suppressed in the case of the modulation Δν=20 GHz used for the detection of the absorption line of the gas component of interest, i.e., the etalon 5 is largely invisible for the 2f detection in the case of Δν/FSR=0.05 and the absorption line is detected in an undisturbed manner.

The control device 13 shown in FIG. 1 controls the amplitude of the modulation signal 11 in such a way that the wavelength of the light 4, which wavelength is tuned periodically in accordance with the current-time function 9, is modulated alternately with a first modulation amplitude Δν=2 GHz for detection of the absorption line of the gas component of interest and with a second modulation amplitude Δν=20 GHz for the wavelength stabilization of the semiconductor laser 3. The wavelength stabilization can be effected as required or after a predefined number of successive measurements of the absorption line.

As explained above with reference to FIG. 2, the transmission spectrum of an etalon has a periodic profile if the free spectral range FSR is less than the tuning range of the semiconductor laser 3. The detection of a maximum or minimum required for the wavelength stabilization is made more difficult as a result.

In an alternative variant relative to the solution described above, the etalon structure 5 contains at least two different etalons, the free spectral ranges of which are chosen to be in each case less than the tuning range and furthermore such that the amplitude of the transmission function of each of the etalons in the case of the first modulation amplitude is at least approximately zero. The first three zeros of the Bessel function $J_2$ are attained if 0.83, 1.34 and 1.85 times the free spectral range of the etalon are respectively used for the modulation amplitude Δν. Proceeding from the modulation Δν=2 GHz used for the detection of the absorption line of the gas component of interest, this results in the following corresponding free spectral ranges FSR=2.4 GHz, 1.49 GHz and 1.08 GHz, respectively. An etalon structure 5 consisting of three etalons having the free spectral ranges mentioned above is largely invisible to the 2f detection in the case of the first modulation amplitude Δν=2 GHz, such that the absorption line is detected largely in an undisturbed manner.

Figure 5:
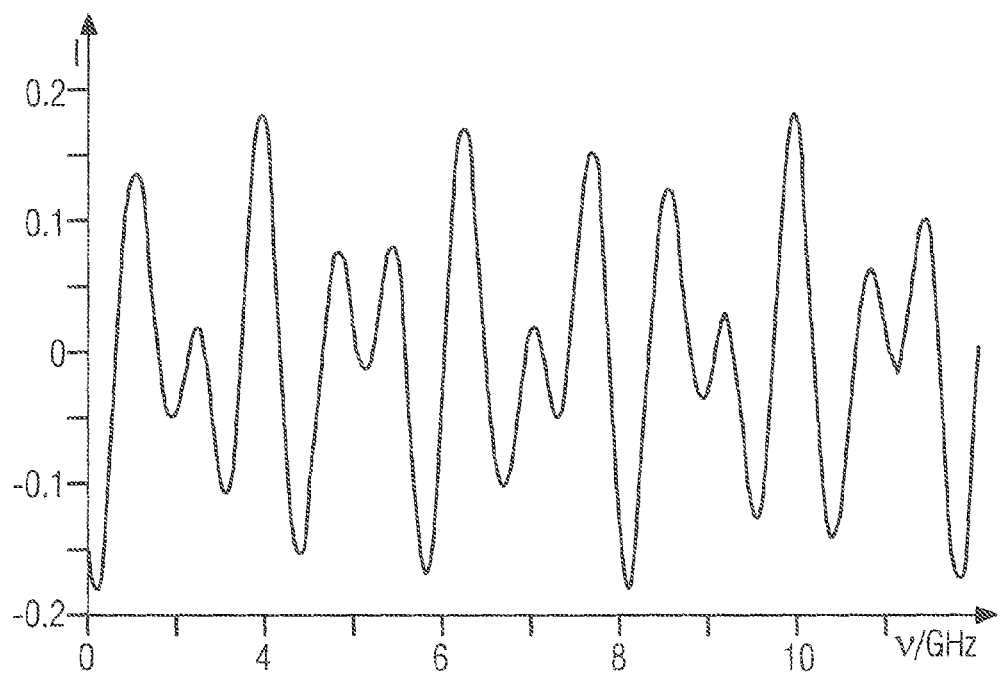
FIG. 5 shows one example of the transmission spectrum of an etalon structure comprising three etalons in accordance with one embodiment of the present invention.

FIG. 5 shows the transmission spectrum of the etalon structure 5 consisting of the three etalons in the case of the second modulation amplitude used for the wavelength stabilization, e.g., Δν=15 GHz. Since the zeros of the Bessel function $J_2$ are not rational multiples of one another, the transmission spectrum resulting from the superimposition of the transmission spectra of individual etalons is no longer periodic, as a result of which the detection of a maximum or minimum required for the wavelength stabilization is facilitated. This is already the case for two etalons. As a result of manufacturing tolerances, however, it may be expedient to use a larger number of etalons in order to increase the irregularity of the resulting transmission spectrum. There are many possibilities for realizing an etalon structure consisting of a plurality of etalons. In this regard, in the case of the etalon 5 shown in FIG. 1, each of the two windows 19, 20 already forms a dedicated etalon.

In the method and laser spectrometer according to the invention, therefore, the transmission spectrum of the etalon structure is detected in the same way as the absorption line of the gas component of interest, i.e., according to the principle of "second harmonic detection." In this case, however, the modulation amplitude, and thus the frequency or wavelength excursion of the light generated, is adapted in each case to the spectral width of the etalon 5 or of the absorption line. Since, on account of the frequency or wavelength modulation, the level of the resulting 2f detector signal is dependent on the ratio of the modulation to the spectral width, it is possible, according to the invention, for the gas mixture containing the gas component to be measured and an etalon structure to be arranged jointly one behind the other in the light path of the laser spectrometer and for the respective influence of the absorption line to be measured and that of the etalon on the detector signal to be controlled using the modulation amplitude such that the signal component generated by the absorption line to be measured is distinguishable from the signal component generated by the etalon.

The series of detailed descriptions set forth above are only specific descriptions directed to the feasible embodiments of the present invention, and are not intended to limit the scope of protection of the present invention; and all the equivalent embodiments or modifications made without departing from the technical spirit of the present invention shall be included in the scope of protection of the present invention.

What is claimed is:

1. A method for operating a laser spectrometer, comprising:
    passing light of a wavelength-tunable semiconductor laser through a gas mixture containing a gas component to be measured and through an etalon structure onto a detector;
    periodically varying an injection current of the semiconductor laser based on a predefined current-time function in order to tune the wavelength ($\lambda$) of the semiconductor laser in a tuning range using a specific absorption line of the gas component;
    modulating the current-time function with a modulation signal having a frequency and a first modulation amplitude and a second modulation amplitude, wherein the first modulation amplitude is adapted to the full width at half maximum of the absorption line and the second modulation amplitude is greater by a multiple of the first modulation amplitude, and wherein the first and second modulation amplitudes are used alternately; and
    evaluating a detector signal generated by the detector for determining (1) the concentration of the gas component to be measured in the gas mixture upon the modulation with the first modulation amplitude and (2) the wavelength stabilization of the semiconductor laser upon the modulation with the second modulation amplitude at the second harmonic of the frequency,
    wherein the etalon structure contains one of (1) a single etalon, the free spectral range (FSR) of which is greater than the tuning range and less than double the tuning range and the second modulation amplitude is adapted to the free spectral range (FSR) of the etalon structure and (2) at least two different etalons, the free spectral ranges of which are chosen in each case to be less than the tuning range such that the amplitude of the transmission function of each of the etalons, the dependence of which on the modulation amplitude approximately follows a Bessel function of the first kind and second order, is at least approximately zero at the first modulation amplitude.

2. A laser spectrometer comprising:
    a wavelength-tunable semiconductor laser;
    a detector for generating a detector signal;
    a controllable current generation apparatus for periodically modulating an injection current of the semiconductor laser; and
    an evaluation device for evaluating the detector signal,
    wherein a gas mixture containing a gas component to be measured and an etalon structure lie in a light path between the semiconductor laser and the detector,
    wherein the controllable current generation apparatus is configured to vary the injection current in a tuning range based on a predefined current-time function, which is additionally modulated with a frequency and, in alternation, a first and second amplitudes,
    wherein the evaluation device is configured to evaluate the detector signal for determining (1) the concentration of the gas component to be measured in the gas mixture upon the modulation with the first modulation amplitude and (2) the wavelength stabilization of the semiconductor laser upon the modulation with the second modulation amplitude at the second harmonic of the frequency,
    wherein the etalon structure contains one of (1) a single etalon, the free spectral range (FSR) of which is greater than the tuning range and less than double the tuning range, and the second modulation amplitude is adapted to the free spectral range (FSR) of the etalon structure and (2) at least two different etalons, the free spectral ranges of which are chosen in each case to be less than the tuning range such that the amplitude of the transmission function of each of the etalons, the dependence of which on the modulation amplitude approximately follows a Bessel function of the first kind and second order, is at least approximately zero at the first modulation amplitude.

* * * * *